United States Patent
Yamamoto

(10) Patent No.: US 8,360,967 B2
(45) Date of Patent: Jan. 29, 2013

(54) DISTAL END OPTICAL UNIT FOR ELECTRONIC ENDOSCOPE

(75) Inventor: Kazuyuki Yamamoto, Saitama (JP)

(73) Assignee: Hoya Corporation, Tokyo (JP)

( * ) Notice: Subject to any disclaimer, the term of this patent is extended or adjusted under 35 U.S.C. 154(b) by 1128 days.

(21) Appl. No.: 11/843,981

(22) Filed: Aug. 23, 2007

(65) Prior Publication Data

US 2008/0080051 A1 Apr. 3, 2008

(30) Foreign Application Priority Data

Sep. 28, 2006 (JP) ................. 2006-263838

(51) Int. Cl.
- *A61B 1/06* (2006.01)
- *A61B 1/00* (2006.01)
- *A61B 1/04* (2006.01)

(52) U.S. Cl. .......... 600/176; 600/133; 600/109

(58) Field of Classification Search ........ 600/109, 600/129, 130, 133, 176, 167, 168, 175; 348/65, 348/340

See application file for complete search history.

(56) References Cited

U.S. PATENT DOCUMENTS

| | | | | |
|---|---|---|---|---|
| 4,706,653 A * | 11/1987 | Yamamoto | ............ | 600/175 |
| 4,856,495 A * | 8/1989 | Tohjoh et al. | ............ | 600/175 |
| 4,860,732 A * | 8/1989 | Hasegawa et al. | ........ | 600/109 |
| 5,050,584 A * | 9/1991 | Matsuura | ............ | 600/130 |
| 5,305,736 A * | 4/1994 | Ito | ............ | 600/109 |
| 5,480,398 A * | 1/1996 | Eggers | ............ | 606/29 |
| 5,547,457 A * | 8/1996 | Tsuyuki et al. | ............ | 600/175 |
| 5,609,561 A * | 3/1997 | Uehara et al. | ............ | 600/112 |
| 5,718,663 A * | 2/1998 | Wulfsberg | ............ | 600/176 |
| 5,810,713 A * | 9/1998 | Rondeau et al. | ............ | 600/133 |
| 5,993,381 A * | 11/1999 | Ito | ............ | 600/131 |
| 6,142,930 A * | 11/2000 | Ito et al. | ............ | 600/109 |
| 6,206,825 B1 * | 3/2001 | Tsuyuki | ............ | 600/182 |
| 6,547,721 B1 * | 4/2003 | Higuma et al. | ............ | 600/133 |
| 6,547,722 B1 * | 4/2003 | Higuma et al. | ............ | 600/133 |
| 6,554,767 B2 * | 4/2003 | Tanaka | ............ | 600/175 |
| 6,572,537 B2 * | 6/2003 | Futatsugi et al. | ............ | 600/133 |
| 6,582,360 B1 * | 6/2003 | Torii | ............ | 600/129 |
| 6,767,322 B1 * | 7/2004 | Futatsugi et al. | ............ | 600/133 |
| 6,773,392 B2 * | 8/2004 | Kikuchi et al. | ............ | 600/109 |
| 6,796,939 B1 * | 9/2004 | Hirata et al. | ............ | 600/179 |
| 7,267,647 B2 * | 9/2007 | Okada et al. | ............ | 600/166 |

(Continued)

FOREIGN PATENT DOCUMENTS

| | | |
|---|---|---|
| JP | 2000-060793 | 2/2000 |
| JP | 2000-115594 | 4/2000 |

(Continued)

*Primary Examiner* — Philip R Smith
*Assistant Examiner* — William Chou
(74) *Attorney, Agent, or Firm* — Greenblum & Bernstein, P.L.C.

(57) ABSTRACT

A distal end optical unit for an electronic endoscope includes a first supporting tube configured to support an image sensor therein, a second supporting tube, and a third supporting tube configured to support an objective optical system. The first supporting tube includes a first open end, a first sealed end that is hermetically sealed, and a metal-covered inner circumferential surface. The second supporting tube includes a second open end, a second sealed end that is hermetically sealed with a cover lens, and a metal-covered outer circumferential surface. The third supporting tube has an inner circumferential surface with a low reflectivity. The third supporting tube is fitted into the second supporting tube. The second open end of the second supporting tube is fitted into and hermetically joined to the first open end of the first supporting tube.

16 Claims, 5 Drawing Sheets

U.S. PATENT DOCUMENTS

| | | | |
|---|---|---|---|
| 7,679,276 B2* | 3/2010 | Blondia et al. | 313/252 |
| 7,695,431 B2* | 4/2010 | Okada | 600/176 |
| 7,713,189 B2* | 5/2010 | Hanke | 600/109 |
| 7,896,802 B2* | 3/2011 | Otawara | 600/157 |
| 2002/0026093 A1* | 2/2002 | Ooyatsu | 600/118 |
| 2002/0128539 A1* | 9/2002 | Higuma et al. | 600/133 |
| 2003/0170024 A1* | 9/2003 | Nishioka et al. | 398/43 |
| 2003/0216614 A1* | 11/2003 | Sawai | 600/110 |
| 2004/0067664 A1* | 4/2004 | Proudfoot et al. | 439/68 |
| 2005/0020877 A1* | 1/2005 | Ishihara et al. | 600/109 |
| 2005/0192477 A1* | 9/2005 | Forster et al. | 600/133 |
| 2006/0173242 A1* | 8/2006 | Navok et al. | 600/133 |
| 2007/0004964 A1 | 1/2007 | Ogino et al. | |
| 2007/0008407 A1 | 1/2007 | Yamamoto et al. | |
| 2007/0010706 A1 | 1/2007 | Yamamoto et al. | |
| 2007/0027360 A1* | 2/2007 | Mitsuya | 600/129 |
| 2007/0118019 A1* | 5/2007 | Mitani et al. | 600/176 |
| 2007/0142711 A1* | 6/2007 | Bayer et al. | 600/175 |
| 2007/0185384 A1* | 8/2007 | Bayer et al. | 600/129 |
| 2007/0191684 A1* | 8/2007 | Hirata | 600/179 |
| 2007/0293725 A1* | 12/2007 | Hasegawa | 600/168 |
| 2008/0039693 A1* | 2/2008 | Karasawa | 600/175 |
| 2008/0132760 A1* | 6/2008 | Takeuchi | 600/129 |
| 2009/0124856 A1* | 5/2009 | Otawara | 600/129 |
| 2010/0152540 A1* | 6/2010 | Tanoue | 600/175 |

FOREIGN PATENT DOCUMENTS

| | | |
|---|---|---|
| JP | 2006-259054 | 9/2006 |
| JP | 2006-262915 | 10/2006 |

* cited by examiner

DISTAL END OPTICAL UNIT FOR ELECTRONIC ENDOSCOPE

BACKGROUND OF THE INVENTION

The present invention relates to a distal end optical unit for an electronic endoscope that can provide high durability and optical performance.

Recently, in most cases, an endoscope is sterilized in an autoclave (high-temperature high-pressure steam sterilizer) each time the endoscope has been used once. Therefore, the endoscope is required to have durability against sterilization by the autoclave.

To prevent steam generated by the autoclave from entering into an objective lens or an imaging surface of a solid-state image sensor, a distal end optical unit for an electronic endoscope is configured with an objective lens supporting tube in which an optical lens group is fixedly inserted and an image sensor supporting tube in which the solid-state image sensor is fixedly inserted being hermetically joined by soldering or brazing metal-plated portions thereof with melting metal material. Further, an observation port cover lens is attached to a distal end portion of the objective lens supporting tube (for example, Japanese Patent Provisional Publications No. 2000-60793 and No. 2000-115594).

Such a hermetically-sealed joint portion between the objective lens supporting tube and image sensor supporting tube provides high durability against the steam of the autoclave. Thereby, the objective lens group and solid-state image sensor, which are protected inside the hermetically-sealed tubes, are not affected by the steam of the autoclave.

However, when the objective lens supporting tube is metal-plated, peripheral light outside effective light for an endoscope observation image may be incident onto an outer circumferential portion of the objective lens and strongly reflected on an inner circumferential surface of the objective lens supporting tube, causing undesired optical flare and/or ghost.

SUMMARY OF THE INVENTION

The present invention is advantageous in that there can be provided an improved distal end optical unit for an electronic endoscope that can attain high durability against environment in an autoclave and high optical performance to prevent optical flare and ghost.

According to an aspect of the present invention, there is provided a distal end optical unit for an electronic endoscope, which includes a first supporting tube configured to support an image sensor therein, a second supporting tube, and a third supporting tube configured to support an objective optical system. The first supporting tube includes a first open end, a first sealed end that is hermetically sealed, and a metal-covered inner circumferential surface. The second supporting tube includes a second open end, a second sealed end that is hermetically sealed with a cover lens, and a metal-covered outer circumferential surface. The third supporting tube has an inner circumferential surface with a low reflectivity, and is fitted into the second supporting tube. The second open end of the second supporting tube is fitted into and hermetically joined to the first open end of the first supporting tube.

Optionally, the metal-covered inner circumferential surface of the first supporting tube may include a gold surface layer.

Optionally, the first supporting tube may be metal-plated over an entire surface thereof.

Further optionally, the first supporting tube may be double-plated with a gold-plated surface layer on a nickel-plated foundation layer over the entire surface thereof.

Optionally, the first sealed end may be hermetically sealed with the image sensor joined to the metal-covered inner circumferential surface of the first supporting tube by one of soldering and brazing.

Optionally, the metal-covered outer circumferential surface of the second supporting tube may include a gold surface layer.

Optionally, the second supporting tube may be metal-plated over an entire surface thereof.

Still optionally, the second supporting tube may be double-plated with a gold-plated surface layer on a nickel-plated foundation layer over the entire surface thereof.

Optionally, the cover lens may have a metalized surface. In this case, preferably, the second sealed end of the second supporting tube may be hermetically sealed with the metalized surface of the cover lens being joined thereto with low melting tin alloy.

Optionally, the second supporting tube may include a first portion at a side of the second open end, in which the third supporting tube is not fitted, and a second portion in which the third supporting tube is fitted, the first portion having an inner diameter larger than that of the second portion.

Yet optionally, the first portion of the second supporting tube may have an inner circumferential surface covered with black coating material.

Optionally, the second supporting tube may be formed from material with a thermal expansion coefficient as low as that of the cover lens.

Further optionally, the second supporting tube may be formed from iron-nickel-cobalt alloy.

Optionally, the inner circumferential surface of the third supporting tube may be covered with black material.

Still optionally, the third supporting tube may be covered with the black material over an entire surface thereof.

Further optionally, the third supporting tube may be formed from metal material and plated with chrome oxide over the entire surface thereof.

Optionally, the second open end of the second supporting tube may be fitted into and hermetically joined to the first open end of the first supporting tube by one of soldering and brazing.

BRIEF DESCRIPTION OF THE ACCOMPANYING DRAWINGS

DETAILED DESCRIPTION OF THE EMBODIMENTS

Figure 1:
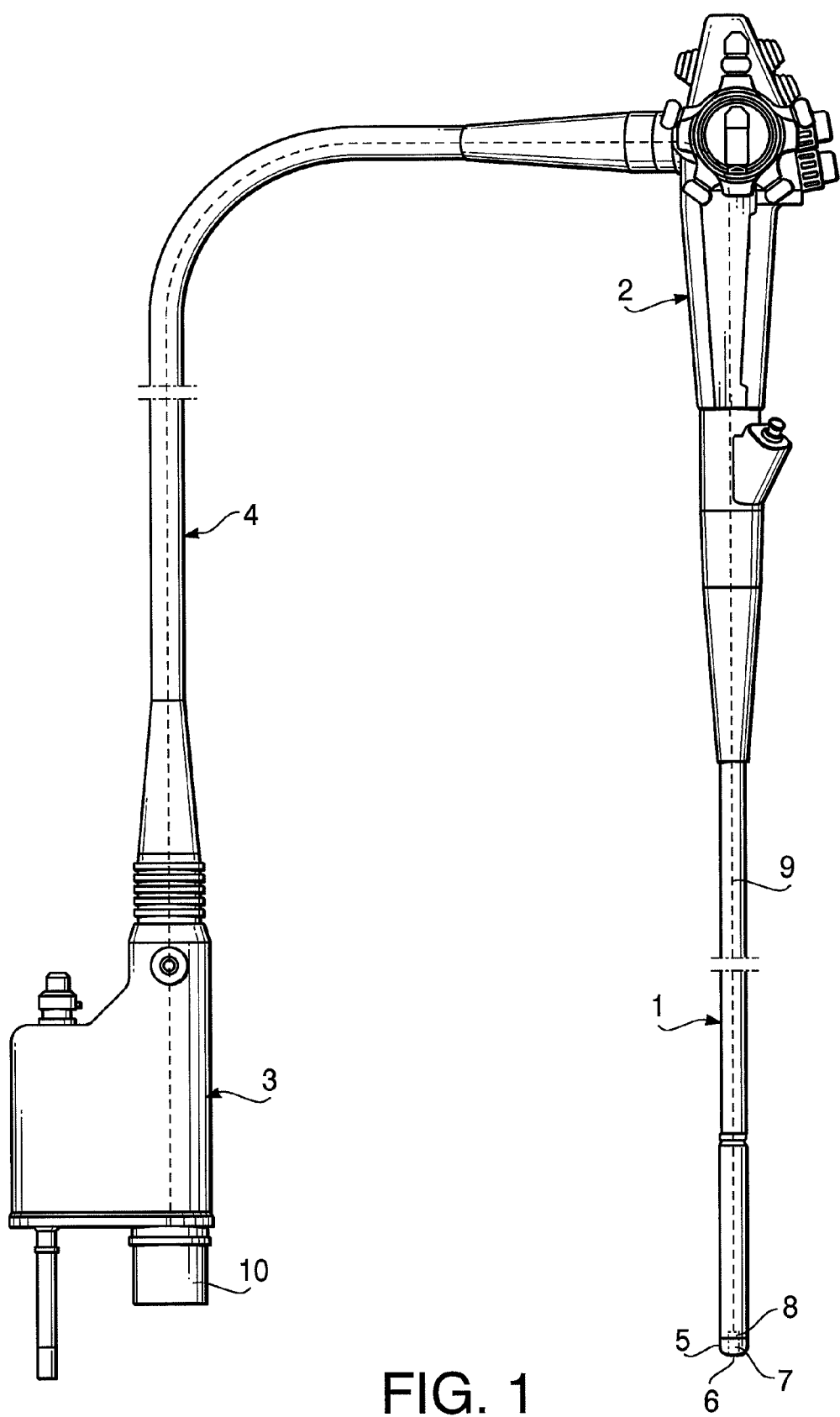
FIG. 1 is an external view showing an entire configuration of an endoscope in an embodiment according to one or more aspects of the present invention.

An embodiment according to aspects of the present invention will be described with reference to the accompanying drawings. FIG. 1 schematically shows an entire configuration of an electronic endoscope. As shown in FIG. 1, an operating portion 2 is linked with a rear anchor of a flexible insertion part 1, and a connector 3 to be connected with a video processor (not shown) is linked with a distal end of a connectable flexible tube 4 extending from neighborhood of an upper end portion at a back surface side of the operating portion 2.

In a distal end body 5 linked with a distal end of the insertion part 1, there is arranged an observation port cover lens 6 alongside of an illumination port cover lens (not shown). Further, an imaging area of a solid-state image sensor 8 is located in an imaging position where an object is imaged by an objective lens system incorporated behind the observation port cover lens 6. A signal outputted from the solid-state image sensor is transmitted to a signal connector portion 10 via a signal cable 9.

Figure 2:
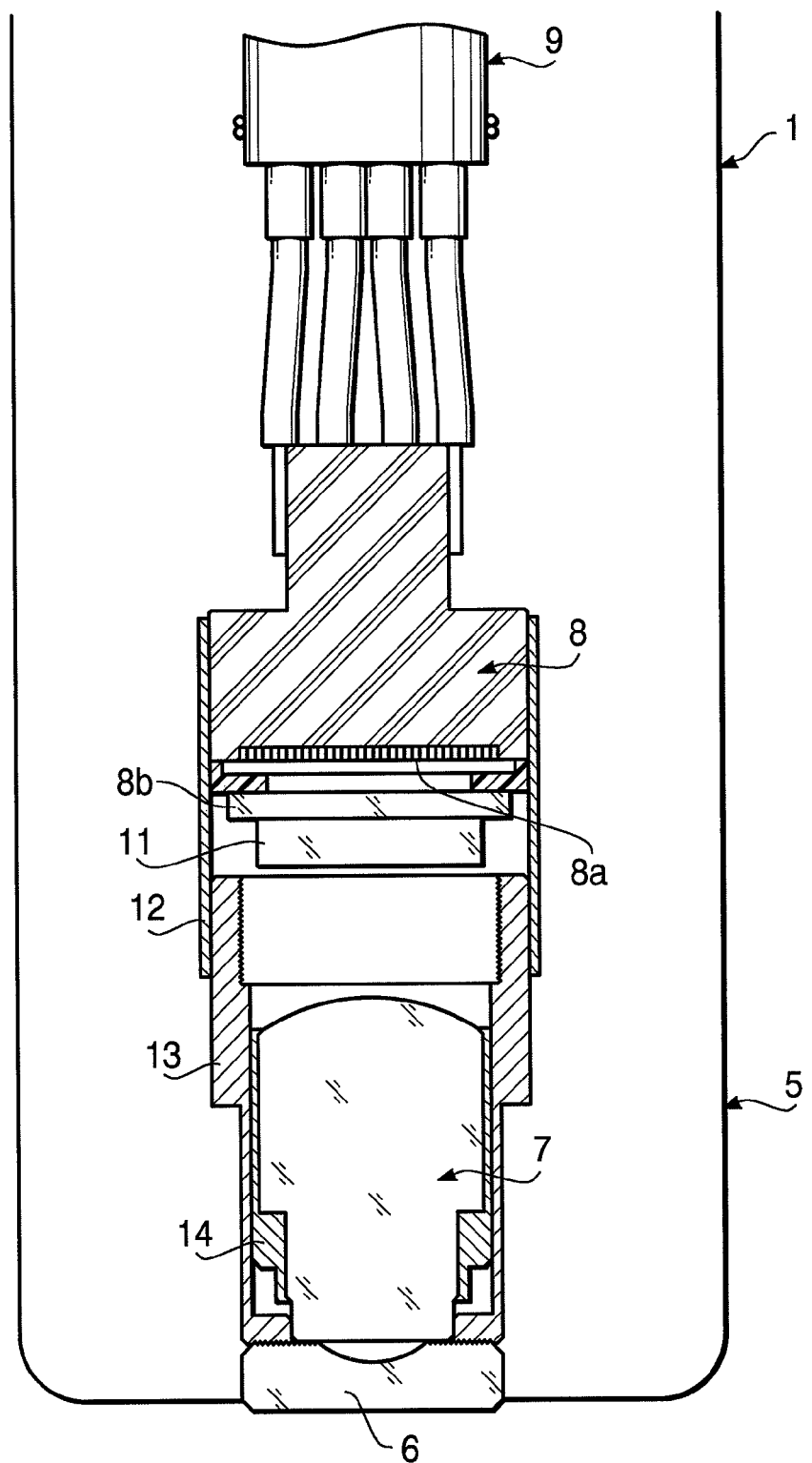
FIG. 2 is a cross-sectional side view of a distal end optical unit for the endoscope in the embodiment according to one or more aspects of the present invention.

FIG. 2 shows a distal end optical unit configured to support the objective lens system 7 and solid-state image sensor 8 in the distal end body 5. An image sensor supporting tube 12 has an open distal end (shown at a lower side in FIG. 2) and a hermetically-sealed rear end. Reference numbers 8a, 8b, and 11 represent the imaging area of the solid-state image sensor 8, a cover glass of the solid-state image sensor 8, and laser cut filter, respectively.

A cover lens supporting tube 13 configured with the observation port cover lens 6 hermetically-attached to a distal end portion thereof has an open rear end. The rear end of the cover lens supporting tube 13 is fitted into an inner circumferential surface at a distal end side of the image sensor supporting tube 12. In addition, an objective lens supporting tube 14 with the objective lens system 7 fixed therein is fitted into an inner circumferential surface of the cover lens supporting tube 13.

Figure 3:
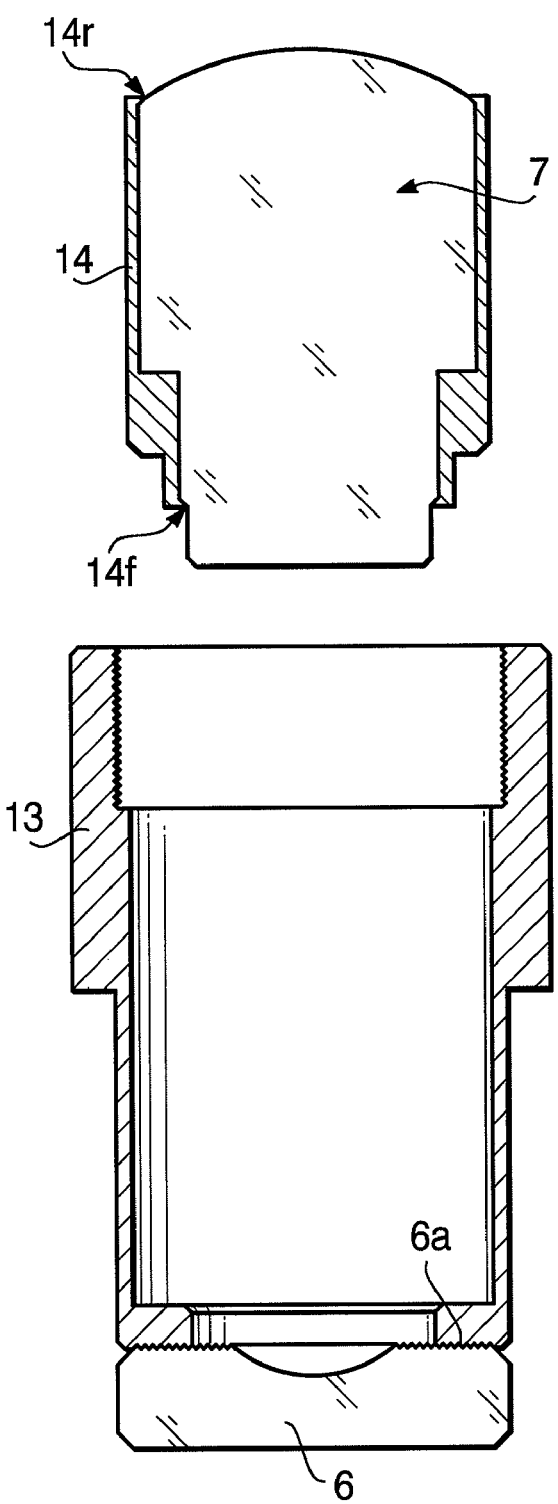
FIGS. 3 to 6 are exploded views in an assembling process for the distal end optical unit in the embodiment according to one or more aspects of the present invention.

Hereinafter, a detailed explanation will be given in accordance with an assembling procedure with reference to FIGS. 3 to 6. As shown in FIG. 3, prior to putting together the cover lens supporting tube 13 and objective lens supporting tube 14, the observation port cover lens 6 is attached onto a distal end surface of the cover lens supporting tube 13, and the objective lens system 7 is fitted into the objective lens supporting tube 14.

The cover lens supporting tube 13 is formed from alloy such as iron-nickel-cobalt alloy with a thermal expansion coefficient as low as that of the observation port cover lens 6. Additionally, the cover lens supporting tube 13 is provided with an entire surface (at least an outer circumferential surface) thereof being double-plated with a surface layer such as a gold-plated layer with high corrosion resistance on a foundation layer such as a nickel-plated layer.

The observation port cover lens 6 attached onto the distal end surface of the cover lens supporting tube 13 is provided with a back surface 6a thereof being metalized in a widely known method. The back surface 6a of the observation port cover lens 6 is hermetically joined to the distal end surface of the metal-plated cover lens supporting tube 13 with low melting tin alloy.

The objective lens supporting tube 14 is formed from metal material and covered with matte black plating material such as chrome oxide over an entire surface (at least an inner circumferential surface) thereof. Accordingly, the inner circumferential surface of the objective lens supporting tube 14 has an extremely low reflectivity.

The objective lens system 7 with a plurality of lenses, simply shown as a single unit in FIG. 3, is fixed in the objective lens supporting tube 14 by calking a front end portion 14f and rear end portion 14r inward. However, in this regard, the objective lens system 7 may be adhered and fixed in the objective lens supporting tube 14.

Figure 4:
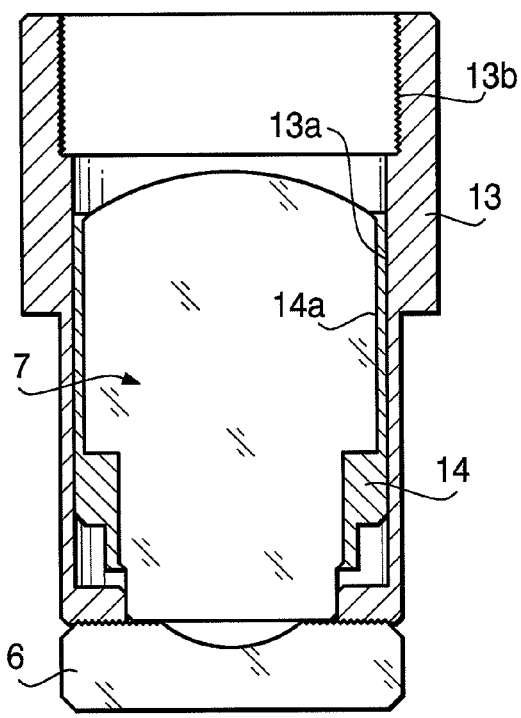

As shown in FIG. 4, the objective lens supporting tube 14 with the objective lens system 7 fitted thereinto is fitted backward into an inner circumferential surface 13a of the cover lens supporting tube 13 with the observation port cover lens 6 attached onto the distal end surface thereof, and fixed in the inner circumferential surface 13a with adhesive material.

In such a state, it is not the inner circumferential surface 13a of the metal-plated cover lens supporting tube 13 but an inner circumferential surface 14a of the black plated objective lens supporting tube 14 that faces an outer circumferential surface of the objective optical system 7. Hence, a ray directed to the outer circumferential surface of the objective optical system 7 from the inside thereof is hardly reflected on the outer circumferential surface thereof.

Further, although an inner circumferential surface 13b at a rear end portion of the cover lens supporting tube 13 is metal-plated (gold-plated) in the same manner as the other portions of the cover lens supporting tube 13, it is possible to prevent a ray passing through the objective lens system 7 from being incident onto the inner circumferential surface 13b by enlarging an inner diameter within the inner circumferential surface 13b. In addition, it is easy to apply black coating material only onto the inner circumferential surface 13b such that the surface 13b can serve as an anti-reflecting surface. When only the inner diameter within the inner circumferential surface 13b is enlarged, it is possible to apply the black coating material onto an exact range of the inner circumferential surface 13b.

Figure 5:
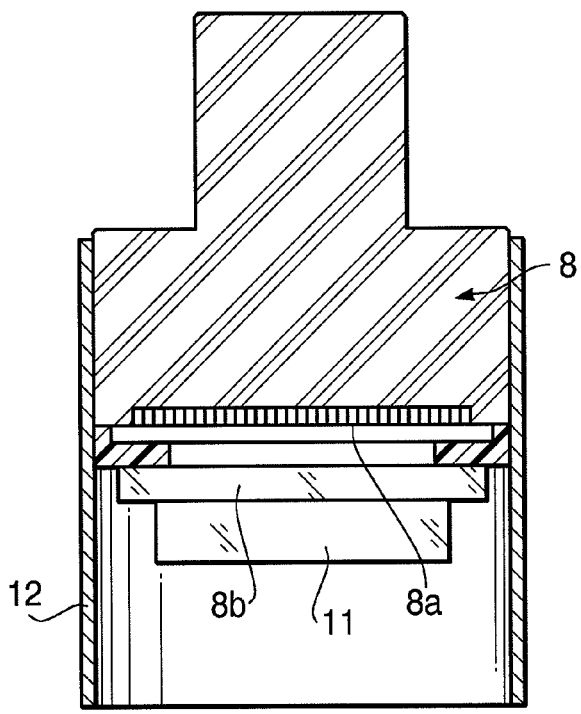

As shown in FIG. 5, the solid-state image sensor 8 is formed in a shape of a block with a portion other than the imaging area 8a being surrounded by insulating material such as ceramics, and hermetically joined to the inner circumferential surface at a rear end portion (at an upper side in FIG. 5) of the image sensor supporting tube 12 by soldering or brazing.

The image sensor supporting tube 12 formed in a shape of a simple tube from metal material is double-plated with a surface layer such as a gold-plated layer with high corrosion resistance on a foundation layer such as a nickel-plated layer over an entire surface thereof (at least the inner circumferential surface).

Figure 6:
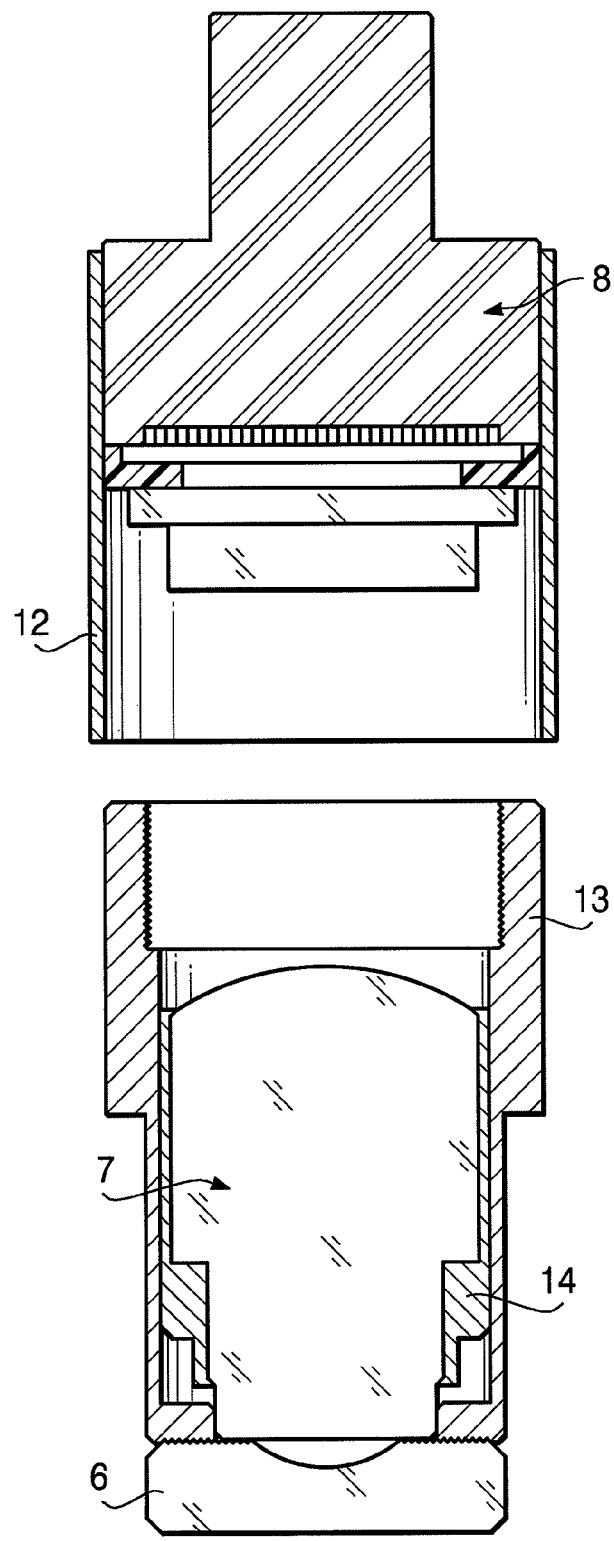

As shown in FIG. 6, the open distal end portion of the image sensor supporting tube 12 and the open rear end portion of the cover lens supporting tube 13 are caused to coaxially face each other. Then, as shown in FIG. 2, the open rear end portion of the cover lens supporting tube 13 is fitted into the open distal end portion of the image sensor supporting tube 12. The image sensor supporting tube 12 and the cover lens supporting tube 13 are hermetically joined with gold-plated surfaces thereof at a fitted portion being connected by soldering or brazing.

Thus, a space where there are arranged components such as the imaging area 8a of the solid-state image sensor 8 and objective optical system 7 is hermetically sealed by soldering or brazing such that the objective optical system 7 and the imaging area 8a of the solid-state image sensor 8 therein are not affected by environment in the autoclave.

In addition, the peripheral light advancing to the outer circumferential surface of the objective optical system 7 is hardly reflected by portions of the objective lens supporting tube 14 onto which the peripheral light is likely to be incident, which are covered with the matte black plating material such as chrome oxide. Therefore, it is possible to prevent optical flare and ghost.

The present disclosure relates to the subject matter contained in Japanese Patent Application No. P2006-263838, filed on Sep. 28, 2006, which is expressly incorporated herein by reference in its entirety.

What is claimed is:

1. A distal end optical unit for an electronic endo scope, comprising:

a first supporting tube configured to support an image sensor therein;
a second supporting tube; and
a third supporting tube configured to support an objective optical system,
wherein the first supporting tube includes:
   a first open end provided at a distal end thereof;
   a first sealed end provided at a proximal end thereof that is hermetically sealed; and
   a metal-covered inner circumferential surface,
wherein the second supporting tube includes:
   a second open end provided at a proximal end thereof;
   a second sealed end provided at a distal end thereof that is hermetically sealed with a cover lens; and
   a metal-covered outer circumferential surface,
wherein the image sensor is entirely housed inside the first supporting tube in an axial direction of the first supporting tube,
wherein the third supporting tube has an inner circumferential surface with a low reflectivity, the third supporting tube being fitted into the second supporting tube,
wherein the second open end provided at the proximal end of the second supporting tube is fitted into and hermetically joined to the first open end provided at the distal end of the first supporting tube,
wherein the second supporting tube is fitted into the first supporting tube and fitted around the third supporting tube such that the third supporting tube is entirely housed inside the second supporting tube in an axial direction of the second supporting tube, and
wherein the second supporting tube includes a first portion at a side of the second open end, in which the third supporting tube is not fitted, and a second portion in which the third supporting tube is fitted, the first portion having an inner diameter larger than that of the second portion.

2. The distal end optical unit according to claim 1, wherein the metal-covered inner circumferential surface of the first supporting tube includes a gold surface layer.

3. The distal end optical unit according to claim 1, wherein the first supporting tube is metal-plated over an entire surface thereof.

4. The distal end optical unit according to claim 3, wherein the first supporting tube is double-plated with a gold-plated surface layer on a nickel-plated foundation layer over the entire surface thereof.

5. The distal end optical unit according to claim 1, wherein the first sealed end is hermetically sealed with the image sensor joined to the metal-covered inner circumferential surface of the first supporting tube by one of soldering and brazing.

6. The distal end optical unit according to claim 1, wherein the metal-covered outer circumferential surface of the second supporting tube includes a gold surface layer.

7. The distal end optical unit according to claim 1, wherein the second supporting tube is metal-plated over an entire surface thereof.

8. The distal end optical unit according to claim 7, wherein the second supporting tube is double-plated with a gold-plated surface layer on a nickel-plated foundation layer over the entire surface thereof.

9. The distal end optical unit according to claim 1, wherein the cover lens has a metalized surface,
   wherein the second sealed end of the second supporting tube is hermetically sealed with the metalized surface of the cover lens being joined thereto with a tin alloy.

10. The distal end optical unit according to claim 1, wherein the first portion of the second supporting tube has an inner circumferential surface covered with black coating material.

11. The distal end optical unit according to claim 1, wherein the second supporting tube is formed from material with a thermal expansion coefficient as low as that of the cover lens.

12. The distal end optical unit according to claim 11, wherein the second supporting tube is formed from iron-nickel-cobalt alloy.

13. The distal end optical unit according to claim 1, wherein the inner circumferential surface of the third supporting tube is covered with black material.

14. The distal end optical unit according to claim 13, wherein the third supporting tube is covered with the black material over an entire surface thereof.

15. The distal end optical unit according to claim 14, wherein the third supporting tube is formed from metal material and plated with chrome oxide over the entire surface thereof.

16. The distal end optical unit according to claim 1, wherein the second open end of the second supporting tube is fitted into and hermetically joined to the first open end of the first supporting tube by one of soldering and brazing.

* * * * *